(12) United States Patent
Kaiser

(10) Patent No.: US 12,325,848 B2
(45) Date of Patent: Jun. 10, 2025

(54) CELL SETTLER APPARATUS SYSTEMS AND METHODS FOR PERFUSION PROCESSES

(71) Applicant: LIFE TECHNOLOGIES CORPORATION, Carlsbad, CA (US)

(72) Inventor: Stephan Kaiser, San Jose, CA (US)

(73) Assignee: Life Technologies Corporation, Carlsbad, CA (US)

( * ) Notice: Subject to any disclaimer, the term of this patent is extended or adjusted under 35 U.S.C. 154(b) by 807 days.

(21) Appl. No.: 17/609,351

(22) PCT Filed: May 13, 2020

(86) PCT No.: PCT/US2020/032765
§ 371 (c)(1),
(2) Date: Nov. 5, 2021

(87) PCT Pub. No.: WO2020/232183
PCT Pub. Date: Nov. 19, 2020

(65) Prior Publication Data
US 2022/0145230 A1   May 12, 2022

Related U.S. Application Data

(60) Provisional application No. 62/848,012, filed on May 15, 2019.

(51) Int. Cl.
*C12M 1/00* (2006.01)
*C12M 1/04* (2006.01)
(Continued)

(52) U.S. Cl.
CPC ............ *C12M 29/10* (2013.01); *C12M 23/24* (2013.01); *C12M 33/22* (2013.01); *C12M 41/12* (2013.01); *C12M 47/10* (2013.01)

(58) Field of Classification Search
None
See application file for complete search history.

(56) References Cited

U.S. PATENT DOCUMENTS

| | | | |
|---|---|---|---|
| 3,709,361 A * | 1/1973 | Miller | C12M 33/22 210/801 |
| 2008/0118974 A1* | 5/2008 | Martin | C12M 29/04 435/297.1 |

(Continued)

FOREIGN PATENT DOCUMENTS

| | | |
|---|---|---|
| CN | 102337200 A | 2/2012 |
| WO | WO-9426384 A1 | 11/1994 |
| WO | WO-2017180814 A1 | 10/2017 |

OTHER PUBLICATIONS

Machine translation of DE-202018000370-U1 provided by Clarivate, original document published May 24, 2018 (Year: 2018).*

(Continued)

*Primary Examiner* — Holly Kipouros

(57) ABSTRACT

The present set of embodiments relate to a system, method, and apparatus for separating cells from a suspension using a gravity driven cell separation device. The apparatus may include a chamber that is separated into a gas compartment and a liquid compartment allowing for transfer of gas through a membrane into the liquid compartment where the cell suspension flows during operation. The embodiments are designed to maximize the gravitational separation effect on the suspension while mitigating the loss of surface area through which gas transfer can occur through a membrane to provide nutrients to cells in the suspension by tilting the cell separation device on two or more axes.

12 Claims, 20 Drawing Sheets

(51) Int. Cl.
*C12M 1/26* (2006.01)
*C12M 1/34* (2006.01)

(56) References Cited

U.S. PATENT DOCUMENTS

| | | |
|---|---|---|
| 2010/0093078 A1 | 4/2010 | Wang et al. |
| 2012/0040453 A1* | 2/2012 | Zal .................... C12M 29/04 |
| | | 435/325 |
| 2014/0099711 A1 | 4/2014 | Shimoni et al. |
| 2019/0210042 A1* | 7/2019 | Kompala ........... B01D 21/0045 |
| 2019/0241917 A1* | 8/2019 | Winterburn ............. C12P 19/62 |
| 2022/0041971 A1* | 2/2022 | Hatanaka ............... C12M 25/16 |

OTHER PUBLICATIONS

PCT/US2020/032765, International Search Report and Written Opinion, Sep. 9, 2020, 11 pages.
PCT/US2020/032765, International Preliminary Report on Patentability, Nov. 25, 2021, 7 pages.

* cited by examiner

400

| Material | Oxygen permeability $\left(\dfrac{mol_{O2} \cdot m}{m^2 \cdot s \cdot Pa}\right)$ |
|---|---|
| Silicone rubber (dimethysilicone) Type #1 | $4.7 \cdot 10^{-15}$ |
| Type #2 | $1.7 \cdot 10^{-13}$ |
| Type #3 | $2.0 \cdot 10^{-13}$ |
| Type #4 | $2.1 \cdot 10^{-13}$ |
| Fluorosilicone | $3.7 \cdot 10^{-14}$ |
| Nitrile silicone | $2.8 \cdot 10^{-14}$ |

FIG. 4

| | Geometry ID | #1 | #2 | #3 | #4 | #5 | #6 | #7 | #8 | #9 |
|---|---|---|---|---|---|---|---|---|---|---|
| Cell settler geometry | Length L (mm) | 200 | 200 | 200 | 200 | 192 | 192 | 192 | 192 | 300 |
| | Width W₁ (mm) | 20 | 50 | 20 | 20 | 40 | 40 | 40 | 7.5 | 200 |
| | Width W₂ (mm) | 20 | 50 | 20 | 20 | 40 | 40 | 40 | 40 | 200 |
| | Thickness H (mm) | 10 | 4 | 6 | 8 | 10 | 10 | 10 | 10 | 10 |
| | Working volume (L) | 0.041 | 0.045 | 0.025 | 0.033 | 0.084 | 0.084 | 0.084 | 0.064 | 0.301 |
| | Inlet Diameter d (mm) | 3 | 3 | 3 | 3 | 4 | 4 | 4 | 4 | 9 |
| | Inlet Length l (mm) | 10 | 10 | 10 | 10 | 10 | 10 | 10 | 10 | 6 |
| | Surface area inlet (10⁻⁶m²) | 6.95 | 7.02 | 6.95 | 6.95 | 12.5 | 12.5 | 12.5 | 12.5 | 60 |
| | Surface area outlet 1 (10⁻⁶m²) | 9.80 | 10.8 | 9.80 | 9.80 | 15 | 15 | 15 | 15 | 60 |
| | Surface area outlet 2 (10⁻⁶m²) | 9.80 | 10.8 | 0.80 | 9.80 | 15 | 15 | 15 | 15 | 60 |
| | Angle α (°) | 55 | 55 | 55 | 55 | 55 | 55 | 55 | 55 | 50 |
| | Angle β (°) | 0 | 0 | 0 | 0 | 0 | 0 | 0 | 0 | 45 |
| | Projected surface area (mm²) | 2458 | 5900 | 2393 | 2425 | 4733 | 4733 | 4733 | 887 | 30167 |
| | Nb. of channels (-) | 1 | 1 | 1 | 1 | 1 | 1 | 1 | 1 | 1 |
| | Side inlets | - | - | - | - | x | - | - | - | - |
| | Multiple inlets | - | - | - | - | x | x | - | x | - |
| | Angled ports | - | - | - | - | - | x | x | x | - |
| | Top inlets | - | - | - | - | - | x | x | - | - |
| Operation parameter | Flow velocity inlet (mm/s) | 5.87 | 5.84 | 5.87 | 5.87 | 1.67 | 1.67 | 1.67 | 1.67 | 1.93 |
| | Flow rate (L/day) | 3.52 | 3.54 | 3.52 | 3.52 | 1.80 | 1.8 | 1.8 | 1.79 | 10.01 |
| | Outflow ratio Fₛ/Fₜₒₜ (-) | 0.5 | 0.5 | 0.5 | 0.5 | 0.5 | 0.5 | 0.5 | 0.5 | 0.5 |

FIG. 13

| | Geometry ID | #10 | #11 | #12 | #13 | #14 | #15 | #16 | #17 | #18 |
|---|---|---|---|---|---|---|---|---|---|---|
| Cell settler geometry | Length L (mm) | 200 | 200 | 192 | 300 | 150 | 200 | 200 | 200 | 200 |
| | Width $W_1$ (mm) | 100 | 200 | 20 | 100 | 100 | 6 | 6 | 4 | 4 |
| | Width $W_2$ (mm) | 100 | 200 | 20 | 100 | 100 | 100 | 100 | 200 | 200 |
| | Thickness H (mm) | 10 | 10 | 10 | 6 | 6 | 10 | 10 | 6 | 6 |
| | Working volume (L) | 0.201 | 0.402 | 0.196 | 0.177 | 0.089 | 0.110 | 0.110 | 0.123 | 0.123 |
| | Inlet Diameter d (mm) | 9 | 9 | 4 | 2 | 2 | 9 | 9 | 2 | 2 |
| | Inlet Length l (mm) | 6 | 6 | 10 | 10 | 10 | 6 | 6 | 10 | 10 |
| | Surface area inlet ($10^{-6} m^2$) | 60 | 60 | 1.25 | 3.1 | 3.1 | 60 | 60 | 3.1 | 3.1 |
| | Surface area outlet 1 ($10^{-6} m^2$) | 60 | 60 | 16 | 3.1 | 3.1 | 60 | 60 | 27.8 | 3.1 |
| | Surface area outlet 2 ($10^{-6} m^2$) | 60 | 60 | 16 | 3.1 | 3.1 | 60 | 60 | 3.1 | 3.1 |
| | Angle α (°) | 50 | 50 | 55 | 45 | 45 | 50 | 50 | 45 | 45 |
| | Angle β (°) | 45 | 45 | 0 | 30 | 30 | 45 | 45 | 30 | 30 |
| | Projected surface area (mm²) | 10765 | 20622 | 2366 | 19432 | 9928 | 5773 | 5773 | 12934 | 12934 |
| | Nb. of channels (-) | 1 | 1 | 4 | 1 | 1 | 1 | 1 | 1 | 1 |
| | Side inlets | - | - | - | - | - | - | - | - | - |
| | Multiple inlets | - | x | x | - | - | - | - | - | - |
| | Angled ports | - | - | - | - | - | - | - | - | - |
| | Top inlets | - | - | - | - | - | - | - | - | - |
| Operation parameter | Flow velocity inlet (mm/s) | 1.93 | 1.93 | 13.3 | 37.5 | 37.5 | 1.93 | 1.93 | 37.5 | 37.5 |
| | Flow rate (L/day) | 10.01 | 10.01 | 14.23 | 10.01 | 10.01 | 10.01 | 10.01 | 10.01 | 10.01 |
| | Outflow ratio $F_s/F_{tot}$ (-) | 0.5 | 0.5 | 0.5 | 0.5 | 0.5 | 0.5 | 0.5 | 0.5 | 0.5 |

FIG. 14

| Design ID | Particle concentration $c_S (\times 10^{-3})$ | | | Particle mass flow rate $\dot{m}_{F,S}(10^{-8} kg/s)$ | | | Separation efficiency SE (-) | |
|---|---|---|---|---|---|---|---|---|
| | Inlet | Outlet #1 | Outlet #2 | Inlet | Outlet #1 | Outlet #2 | CFD (Eq. 5) | PNK (Eq. 9) |
| #1 | 1.80 | 1.07 | 6.25 | 21.6 | 6.5 | 15.3 | 0.70 | 0.60 |
| #2 | 1.80 | 1.85 | 5.14 | 21.8 | 5.2 | 16.8 | 0.76 | 0.73 |
| #3 | 1.80 | 1.35 | 5.04 | 21.8 | 8.3 | 13.6 | 0.62 | 0.59 |
| #4 | 1.80 | 1.35 | 4.64 | 21.6 | 8.2 | 13.5 | 0.62 | 0.59 |
| #5 | 1.80 | 1.37 | 4.22 | 21.6 | 8.0 | 13.6 | 0.63 | 0.68 |
| #6 | 1.80 | 1.28 | 4.46 | 21.6 | 7.7 | 13.9 | 0.64 | 0.68 |
| #7 | 1.80 | 1.31 | 4.79 | 21.6 | 7.8 | 13.8 | 0.64 | 0.68 |
| #8(a) | 1.80 | 1.23 | 4.49 | 21.5 | 7.2 | 14.4 | 0.67 | 0.60 |
| #8(b) | 1.80 | 1.32 | 4.18 | 21.5 | 7.7 | 13.8 | 0.64 | 0.60 |
| #9 | 1.80 | 1.37 | 6.49 | 21.6 | 8.1 | 15.8 | 0.62 | 0.59 |
| #10 | 1.00 | 0.56 | 1.82 | 12.2 | 3.3 | 8.9 | 0.73 | 1.00 |
| #11(a) | 1.00 | 0.62 | 1.85 | 12.2 | 3.7 | 8.5 | 0.70 | 0.92 |
| #11(c) | 1.00 | 0.32 | 2.12 | 12.2 | 1.9 | 10.3 | 0.84 | 1.00 |
| #11(b) | 1.00 | 0.39 | 2.06 | 12.2 | 2.4 | 9.8 | 0.81 | 1.00 |
| #12 | 1.80 | n.a. | n.a. | 21.5 | n.a. | n.a. | n.a. | n.a. |
| #13 | 1.00 | 0.74 | 1.25 | 11.6 | 4.3 | 7.3 | 0.63 | 1.00 |
| #14 | 1.77 | 0.16 | 3.49 | 21.5 | 0.1 | 20.9 | 1.00 | 1.00 |
| #15(d) | 1.77 | 0.55 | 3.11 | 21.5 | 3.4 | 18.7 | 0.84 | 0.89 |
| #15(e) | 1.00 | 0.63 | 1.92 | 12.2 | 3.8 | 8.3 | 0.69 | 0.72 |
| #16(f) | 1.00 | 0.48 | 1.68 | 12.2 | 1.1 | 11.0 | 0.91 | 0.72 |
| #16(f) | 1.00 | 0.63 | 1.85 | 12.2 | 3.8 | 8.3 | 0.68 | 0.72 |
| #17 | 1.00 | 0.60 | 1.91 | 12.2 | 3.6 | 8.6 | 0.70 | 0.72 |
| #18 | 1.77 | 0.73 | 2.90 | 21.5 | 4.4 | 17.3 | 0.80 | 1.00 |

(a)inlet 1, (b)inlet 2, (c)inlet 3, (d)gravity vector rotated, (e)geometry rotated, (f)outlets on opposite sides

FIG. 15

CELL SETTLER APPARATUS SYSTEMS AND METHODS FOR PERFUSION PROCESSES

CROSS-REFERENCE TO RELATED APPLICATIONS

This application is a U.S. 371 of International Application No. PCT/US2020/032765, filed May 13, 2020, which claims priority to U.S. Application No. 62/848,012, filed May 15, 20219. The entire contents of this application are hereby incorporated herein by reference.

BACKGROUND

The bioproduction industry makes use of both batch fed and perfusion processes to culture cells and harvest cell related products. Perfusion methods necessitate a way to siphon off a portion of a cell culture contained within a bioreactor and separate cells from waste which creates a variety of technical hurdles.

Commercially available separation systems include filters which are prone to fouling, acoustics devices that can generate heat that can be harmful to cells, and centrifugation which can generate shear stress that can damage cells.

What is needed is a simple, low-cost system and method that does not suffer from any of the disadvantages described above. Gravity based cell separation devices, systems, and methods are disclosed herein that address the disadvantages of the listed existing technologies in the field.

BRIEF SUMMARY

In one aspect, a perfusion bioproduction system with gravity driven cell separator is disclosed. The system may include a bioreactor and a gravity driven cell separator fluidically connected to the bioreactor. The gravity driven cell separator may include a chamber divided by a membrane into a first compartment and a second compartment, the first compartment adapted to receive a suspension with cells from the bioreactor through an inlet and deliver a clarified liquid to a first outlet and a concentrated suspension to a second outlet, the second compartment adapted to receive a gas from an entry and deliver the gas to an exit, wherein as the gas travels from the entry to the exit at least some gas permeates the membrane to provide the cells with nutrients. In some embodiments, a portion of the concentrated suspension is directed back to the bioreactor and a portion of the clarified liquid is directed to a collection chamber. In some embodiments, a product is harvested from the clarified liquid. In some embodiments, the product includes a protein, antibody, or enzyme. In some embodiments, the bioreactor includes a reaction vessel configured to mix and aerate a suspension, an outlet connected to the reaction vessel and a tube extending from the outlet on the reaction vessel to the inlet of the gravity driven cell separator for sending the suspension from the bioreactor to the gravity driven cell separator, and an inlet connected to the reaction vessel and a tube extending from the inlet of the reaction vessel to the outlet of the gravity driven cell separator for receiving the concentrated suspension from the gravity driven cell separator. In some embodiments, the concentration of cells in the clarified liquid is less than the concentration of cells in the suspension and the concentration of cells in the suspension is less than the concentration of cells in the concentrated suspension. In some embodiments, the membrane is stabilized by a support structure having a plurality of openings and the support structure is joined to the chamber. In some embodiments, the nutrients include oxygen. Some embodiments include a heating element operably connected to the chamber. Some embodiments include a cooling element operably connected to the chamber. Some embodiments include a temperature sensor disposed within the chamber.

In one aspect, gravity driven cell separating system is disclosed. Some embodiments may include a bioreactor, a cell separating device having a first planar face and a second planar face joined by a plurality of sides, wherein the cell separating device is tilted on two axes relative to a gravitational vector, a first chamber formed between the first planar face and a membrane and bounded by the sides, wherein the first chamber includes an inlet adjacent to a side and a first outlet adjacent to a first end of an opposing side and a second outlet adjacent to a second end of the opposing side, wherein a suspension enters the inlet, a clarified liquid exits the first outlet and a concentrated suspension exists the second outlet, and a second chamber formed between the second planar face and the membrane and bounded by the four sides, wherein the second chamber includes an entry adjacent to the opposing side and an exit adjacent to the side, wherein a gas enters the entry and travels to the exit and at least some of the gas passes through the membrane to provide nutrients to cells in the suspension in the first rectangular chamber. In some embodiments, the nutrients include oxygen. In some embodiments, the chamber includes a support structure for supporting the membrane, the support structure having a plurality of openings. In some embodiments, a heating element is positioned on the chamber. In some embodiments, a cooling element is positioned on the chamber. In some embodiments, a sensor detects the temperature within the chamber.

In one aspect, method of concentrating particles in a bioproduction process is disclosed. In some embodiments the steps in the method may include directing a suspension from a bioreactor to a first compartment of a gravity driven particle separator, passing the suspension through the first compartment, and passing a gas from a second compartment of the gravity driven particle separator through a membrane to the first compartment to provide nutrients to cells in the suspension. Some embodiments further comprise the step of concentrating the cells into a concentrated suspension. Some embodiments further comprise the step of directing a clarified liquid to a first outlet and the concentrated suspension to a second outlet. Some embodiments further comprise the step of directing a portion of the concentrated suspension back to the bioreactor. Some embodiments further include the step of cooling the gravity driven particle separator. Some embodiments further include the step of heating the gravity driven particle separator.

In one aspect, a method of setting up and operating a gravity driven cell separator is disclosed. In various embodiments, the steps may include tilting a gravity driven cell separator along a first axis on a Cartesian coordinate system to create an angle of alpha, tilting a gravity driven cell separator along a second axis on a Cartesian coordinate system to create an angle of beta, securing the gravity driven cell separator to a stand at angles alpha and beta, directing a suspension from a bioreactor to a first compartment of the gravity driven particle separator, passing the suspension through the gravity driven particle separator, and passing a gas from a second compartment of the gravity driven particle separator through a membrane to provide nutrients to cells in the suspension. In some embodiments, the nutrients include oxygen.

In one aspect, a method of providing nutrients to cells during sedimentation in a gravity driven cell separator is disclosed. In some embodiments, the steps in the method may include providing a chamber divided by a membrane into a first compartment and a second compartment, directing a suspension having cells from a bioreactor to the first compartment, wherein the suspension travels from a higher elevation to a lower elevation within the first compartment, directing a gas through the second compartment, and passing some of the gas from the second compartment and through the membrane to provide nutrients to cells in the suspension in the first compartment. In some embodiments, the membrane is supported by a support structure having a plurality of openings.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 4 illustrates membrane materials 400 and their associated properties in accordance with various embodiment.

FIGS. 13-15 illustrate cell separator design details 1302 corresponding to the cell separator designs 802 depicted in FIGS. 8-12.

DETAILED DESCRIPTION

Embodiments of systems, methods, and apparatuses for gravity based cell separators used in perfusion and harvest processes are described in the accompanying description and figures. In the figures, numerous specific details are set forth to provide a thorough understanding of certain embodiments. A skilled artisan will be able to appreciate that the systems and methods described herein may be used for a variety of applications including, but not limited to cell culture, perfusion bioprocesses, harvest, and a variety of processes that benefit from cell separation from suspension.

Additionally, the skilled artisan will appreciate that certain embodiments may be practiced without these specific details. Furthermore, one skilled in the art will readily appreciate that the specific sequences in which methods are presented and performed are illustrative and it is contemplated that the sequences may be varied and still remain within the spirit and scope of certain embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in the described various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequence may be varied and still remain within the spirit and scope of the various embodiments.

While preferred embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the apparatuses, systems, and methods described herein may be employed.

Figure 1:
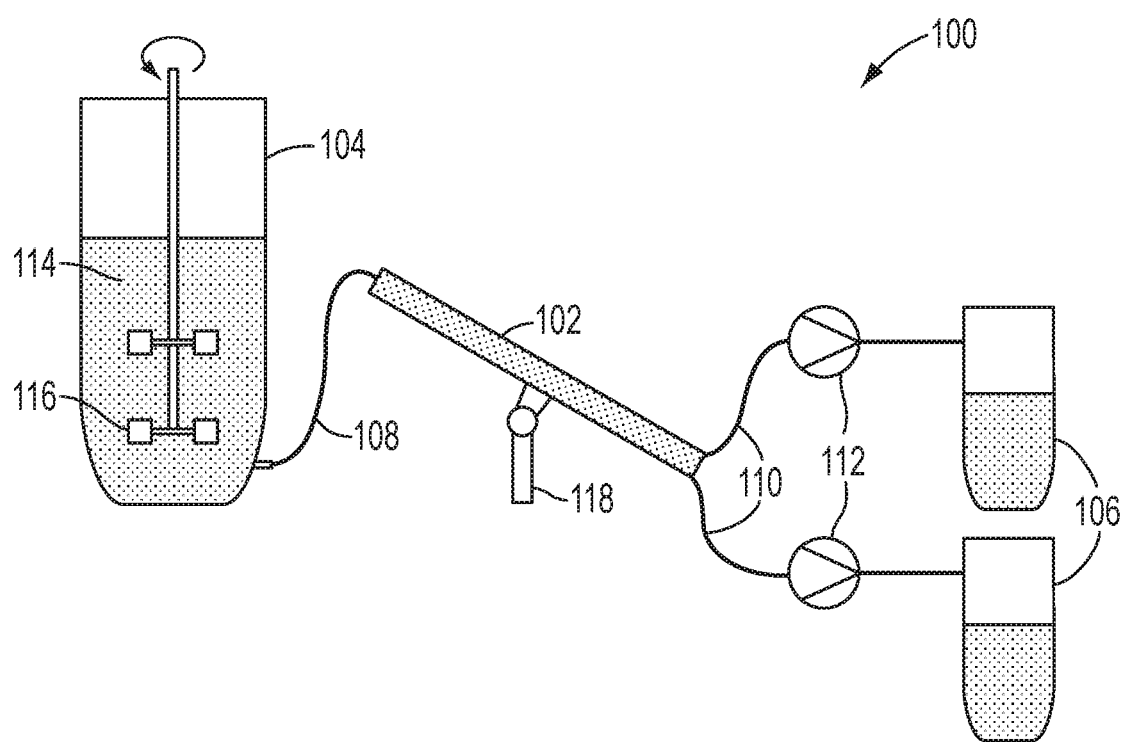
FIG. 1 illustrates a perfusion bioproduction system 100 in accordance with various embodiment.

FIG. 1 illustrates a perfusion bioproduction system 100 according to various embodiments. The perfusion bioproduction system 100 may include a cell separator 102, a bioreactor 104, a collection vessels 106, an entry tube 108, exit tubes 110, pumps 112, a cell suspension 114, a mixer 116, and a stand 118.

In various embodiments, a bioreactor 104 may be fluidically coupled to a cell separator 102 through an entry tube 108 for transfer of a cell suspension 114 containing biological cells. The cell separator 102 may be oriented in such a way that the cell suspension 114 may move through the cell separator 102 using gravity as a motive force. In various embodiments, as the cell suspension 114 travels through the cell separator 102 and a concentrated cell suspension 114 may exit the cell separator 102 through one of the exit tubes 110 and a clarified solution may exit through another one of the exit tubes 110. In some embodiments, the concentrated cell suspension 114 may be returned to the bioreactor 104 to produce more of a desired product with added cell nutrients being provided to the bioreactor 104. In some embodiments, the cells within the cell suspension 114 may travel through the cell separator 102 one, two, three, or many more times depending on the application.

In various embodiments, the bioreactor 104 may include a mixer 116. In various embodiments, the mixer 116 may include a rotatable mixing element, a rocker, an airlift system, or a shaker.

In various embodiments, the cell separator 102 may be secured to a stand 118. The cell separator 102 and stand 118 may be configured such that the cell separator 102 can be secured at various angular orientations along a Cartesian [x, y, and z] coordinate system. In various embodiments, the stand may include a hinge and be rotatable on one or two axes. In some embodiments, the hinge may include a ball joint and be rotatable about any three dimensional axis.

In various embodiments, the collection vessels 106 may be one or more bioreactors. In various embodiments, one or more of the collection vessels 106 may be a chromatography column.

In various embodiments, the cell suspension 114 may include beads and cells may be attached to the beads. In various embodiments, the perfusion bioproduction system 100 may be optimized for separation of beads or cells.

Figure 2:
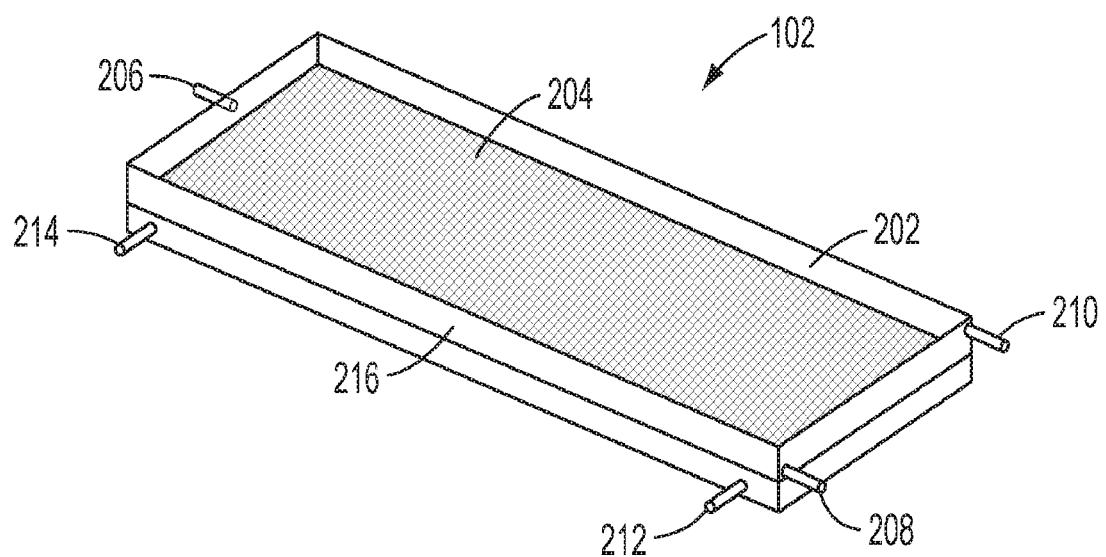
FIG. 2 illustrates an isometric view of a cell separator 102 in accordance with various embodiment.
Figure 3:
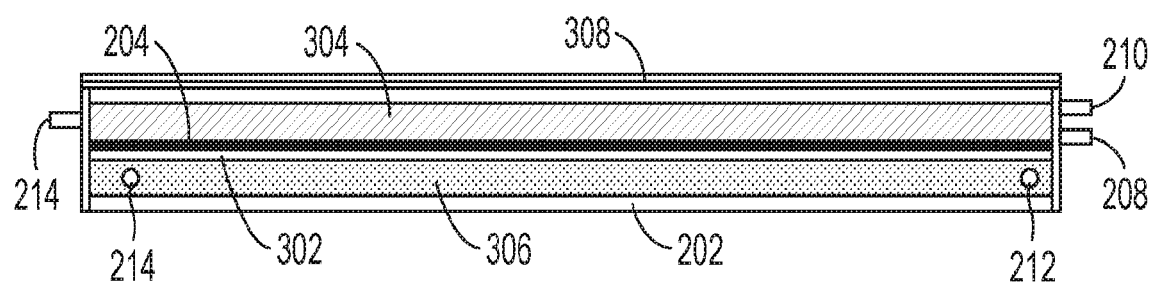
FIG. 3 illustrates a cross sectional view of a cell separator 102 in accordance with various embodiment.

FIG. 2 illustrates an isometric view and FIG. 3 illustrate side view of a cell separator 102 according to various embodiments. The cell separator 102 may include a chamber 202, a membrane 204, a suspension inlet 206, a concentrated suspension outlet 208, a clarified liquid outlet 210, a gas inlet 212, a gas outlet 214, a support structure 302, a gas compartment 306, and a liquid compartment 304.

In various embodiments, the cell separator 102 is designed such that the suspension inlet 206 is elevated above both the concentrated suspension outlet 208 and the clarified liquid outlet 210 and the clarified liquid outlet 210 may be positioned at a greater elevation than the concentrated suspension outlet 208. In some embodiments, such an orientation may be achieved by raising the end of the cell separator 102 having the suspension inlet 206 and rotating the cell separator 102 about its center axis.

In various embodiments, a cell suspension 114 may enter the chamber 202 of the cell separator 102 through the suspension inlet 206 which may then allow the cell suspension 114 to travel downward toward the concentrated suspension outlet 208 and the clarified liquid outlet 210. In various embodiments, having the clarified liquid outlet 210 at a higher elevation than the concentrated suspension outlet 208 outlet assists with cell separation efficiency.

In various embodiments, the gas inlet 212 may be at a lower elevation than the gas outlet 214. Such a configuration allows a gas to travel through the chamber 202 and exit through a gas outlet 214.

In various embodiments, the cell separator 102 may include a chamber 202 that may be separated by a membrane 204 to form a liquid compartment 304 and a gas compartment 306. In various embodiments, at least some of the gas may pass from the gas compartment 306 and through the membrane 204 into the liquid compartment 304 to provide nutrients such as oxygen to cells within the cell suspension 114. In various embodiments, the gas travels against gravity and the cell suspension 114 travels with gravity. In various embodiments, the gas may be provided by a gas supply system (not shown).

In various embodiments, the membrane 204 may be supported by a support structure 302. In various embodiments, the material for the membrane 204 may be selected for a specific application. FIG. 4 illustrates a variety of materials that may be used to create the membrane 204 having different oxygen permeability and mass transfer resistances. A skilled artisan will appreciate that there are many commercially available options for membrane 204 materials.

In various embodiments, a temperature element 308 may be attached to the chamber 202 of the cell separator 102 by weld, adhesion, or any other known method of attachment. The temperature element 308 may include a cooling element, a heating element, and/or a temperature sensor. The temperature element 308 may be part of a feedback system to maintain an optimal temperature for a given application. For example, if the desired result is to lower cellular metabolism the chamber 202 may be kept cool or if the desired result to maintain healthy, growing cells a higher temperature may be maintained that is optimized for cell growth.

In various embodiments, the membrane 204 may be supported by a support structure 302 having a plurality of openings 216 where the openings 216 provide a direct way for the gas compartment 306 and liquid compartment 304 to interact through the membrane 204 and the solid portions of the support structure 302 provide physical support to the membrane 204, thereby, holding the membrane 204 in place.

In various embodiments, the support structure 302 is a contiguous piece of the chamber 202. In various embodiments, the support structure 302 may be welded or adhered to the chamber. In various embodiments, the membrane 204 may rest on the support structure 302. In various embodiments, the membrane 204 may be physically restrained to the support structure 302 or adhered or welded to the support structure 302.

In various embodiments, the membrane 204 allows for mass transfer between the gas compartment 306 and the liquid compartment 304 which may include $CO_2$ removal and $O_2$ addition to the liquid compartment 304. In various embodiments, nutrients can further include oxygen, $CO_2$, or anything else the cells in the cell suspension 114 may require.

Figure 5:
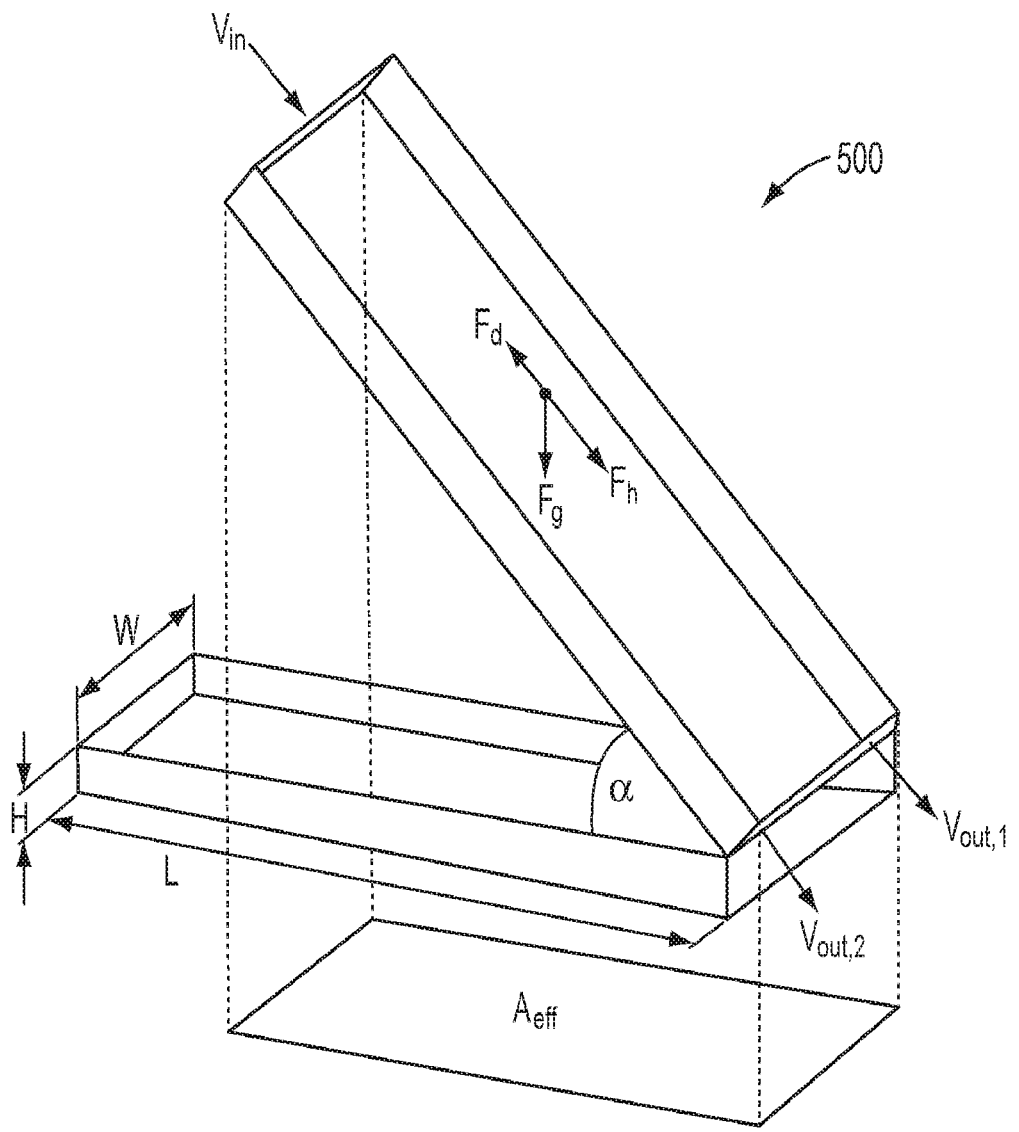
FIG. 5 illustrates a schematic view of a cell separator 500 tilted or rotated about one axis in accordance with one embodiment.

FIG. 5 illustrates a cell separator 500 according to various embodiments. As shown, the cell separator 500 may be tilted at an angle alpha on a length axis (x-axis) which reduces the overall surface area through which gas can permeate the membrane and also increases the gravitation force acting on the cell suspension. As angle alpha increases the cell suspension may move faster through the cell separator 500 to reduce processing time, however, the separation efficiency may be reduced.

Figure 6:
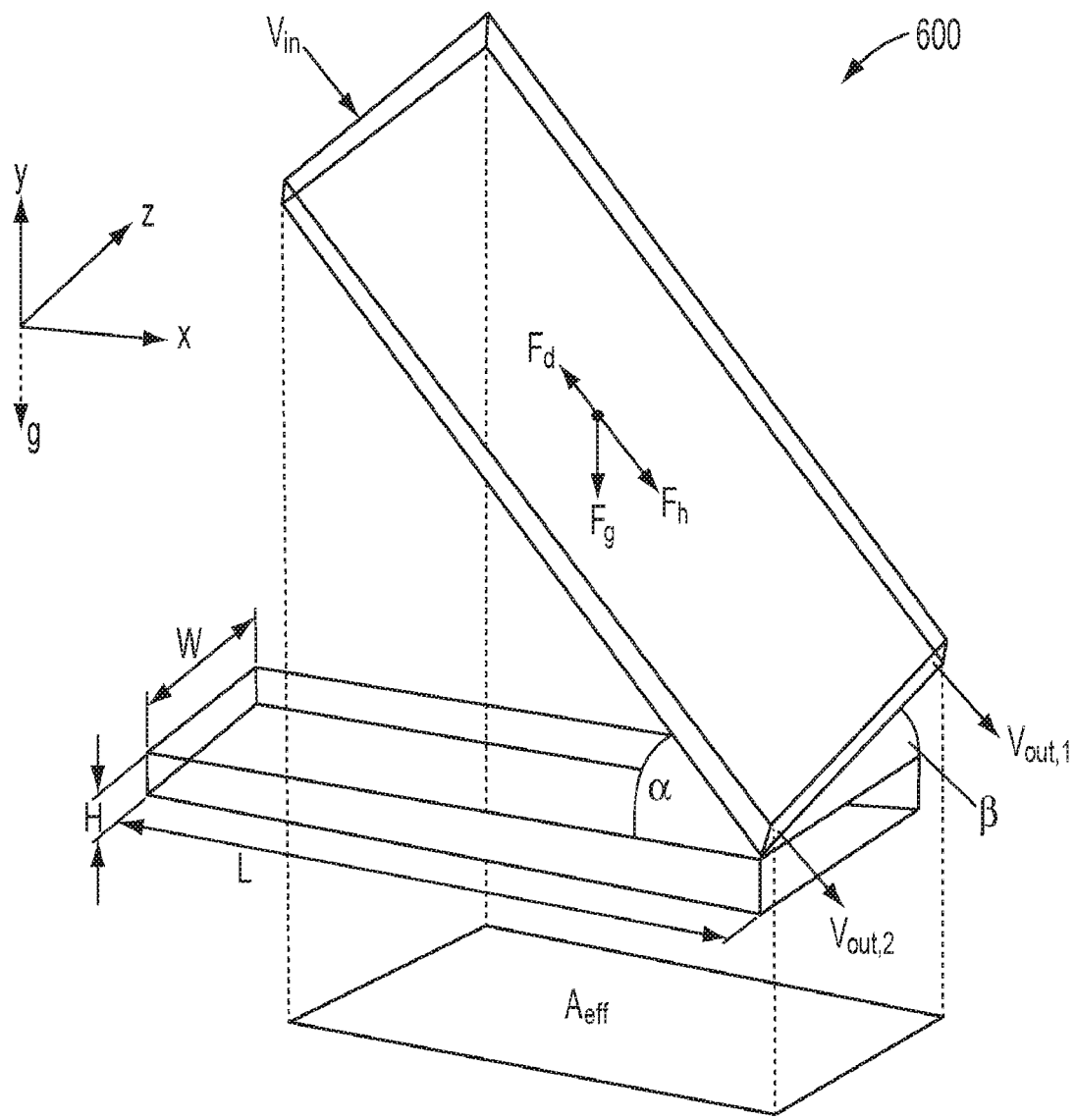
FIG. 6 illustrates a schematic view of a cell separator 600 tilted or rotated about two axes in accordance with one embodiment.

FIG. 6 illustrates a cell separator 600 according to various embodiments. As shown, the cell separator 600 may be tilted at an angle alpha on a length axis (x-axis) and angle beta on a width axis (z-axis). In various embodiments, changing the angle on two axes instead of one may increase the gravitational influence on the cell suspension while mitigating the reduced oxygenation as gas passes through the membrane. In various embodiments, it may be favorable for angle alpha to be greater than angle beta. In various embodiments, angle alpha may be about 45 degrees and angle beta may be about 30 degrees.

Figure 7:
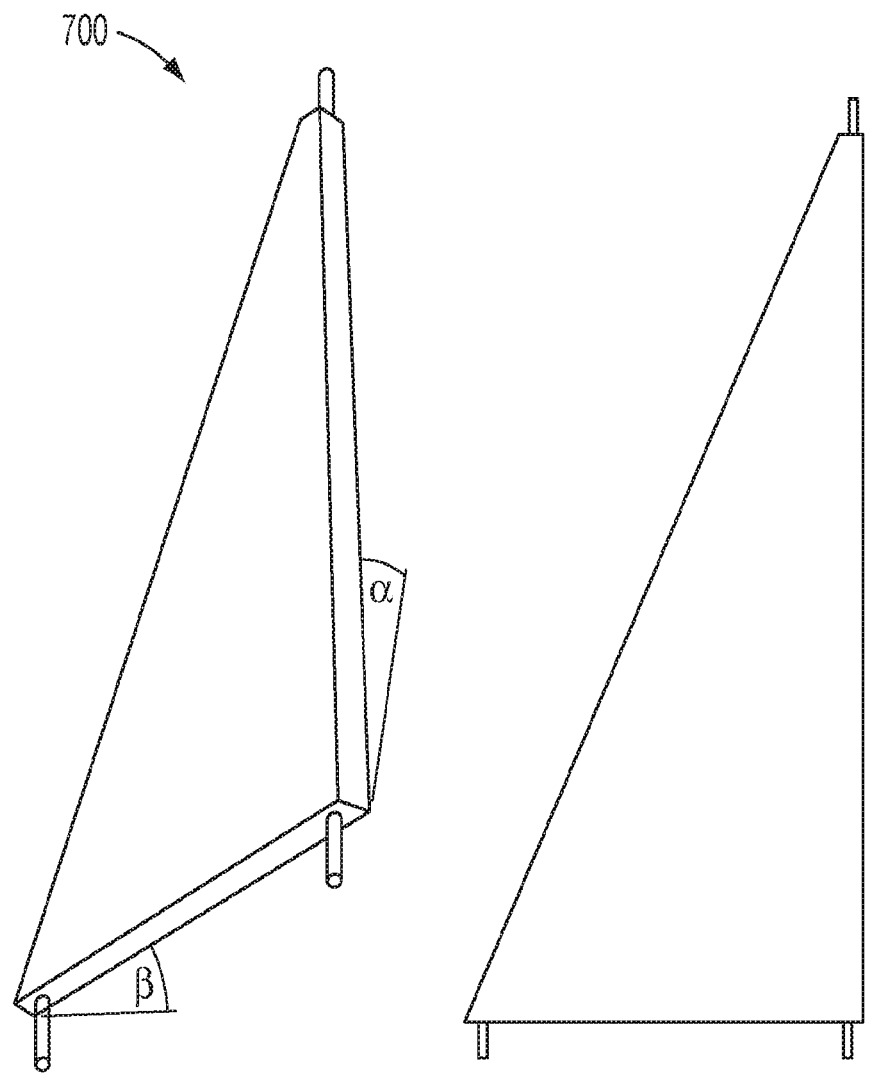
FIG. 7 illustrates a cell separator 700 in accordance with one embodiment.
Figure 8:
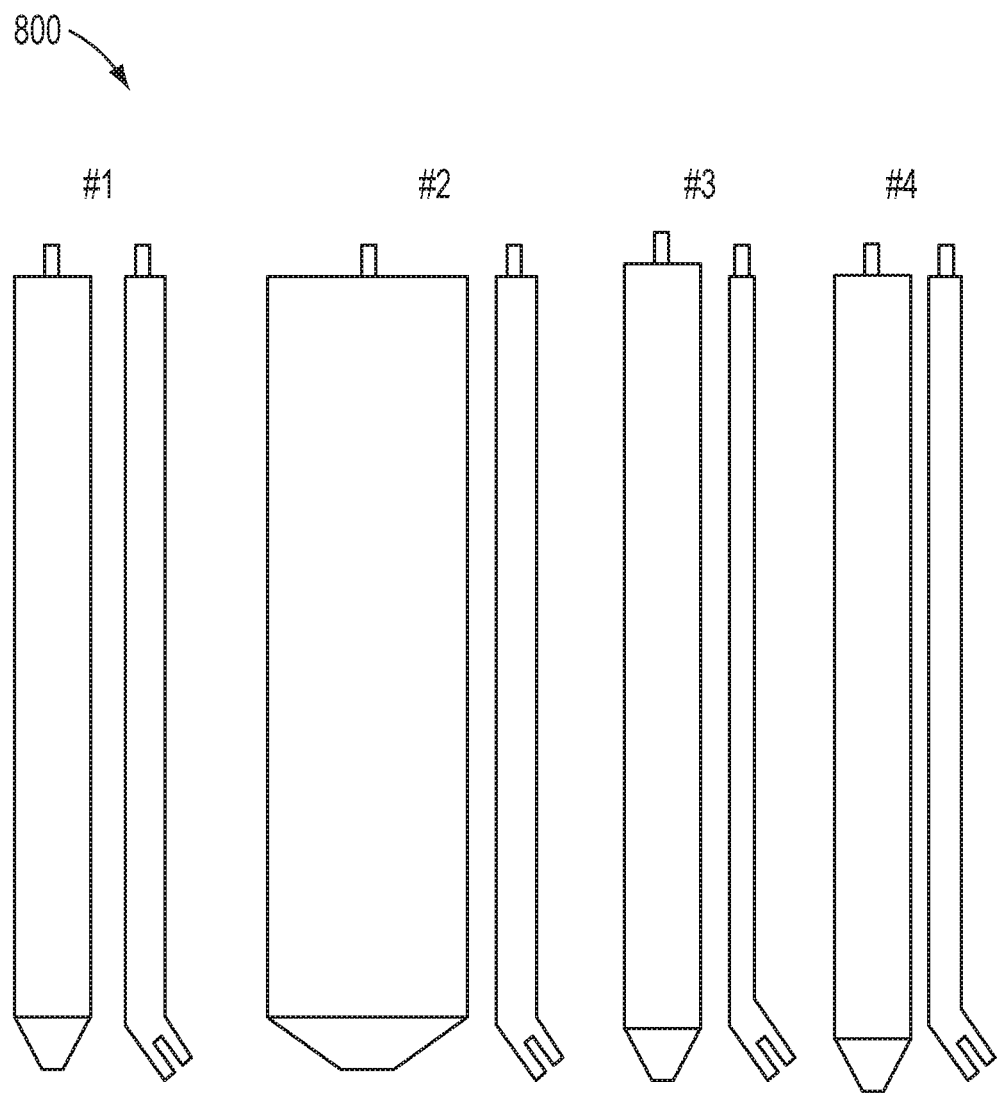
FIGS. 8-12 illustrate a variety of cell separator designs 802 that were investigated.
Figure 9:
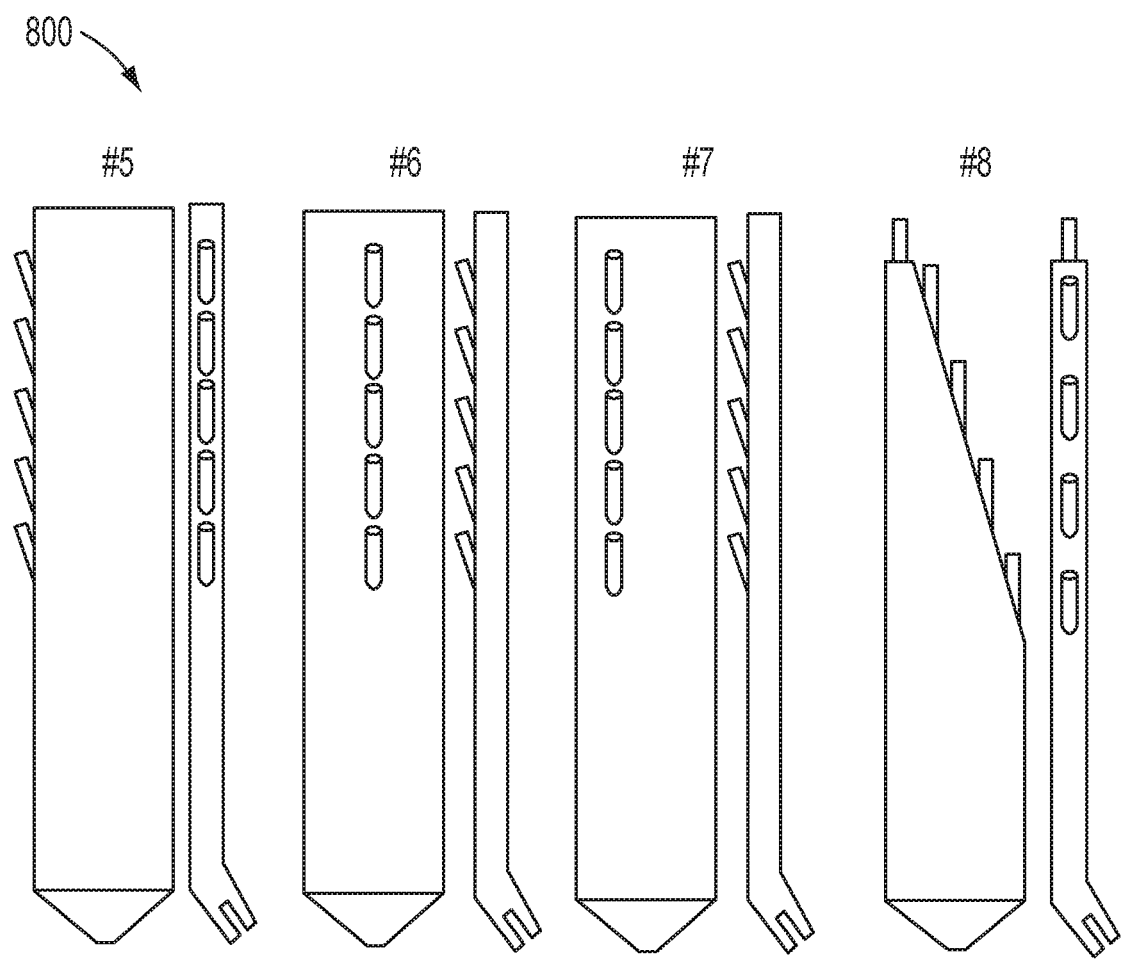
Figure 10:
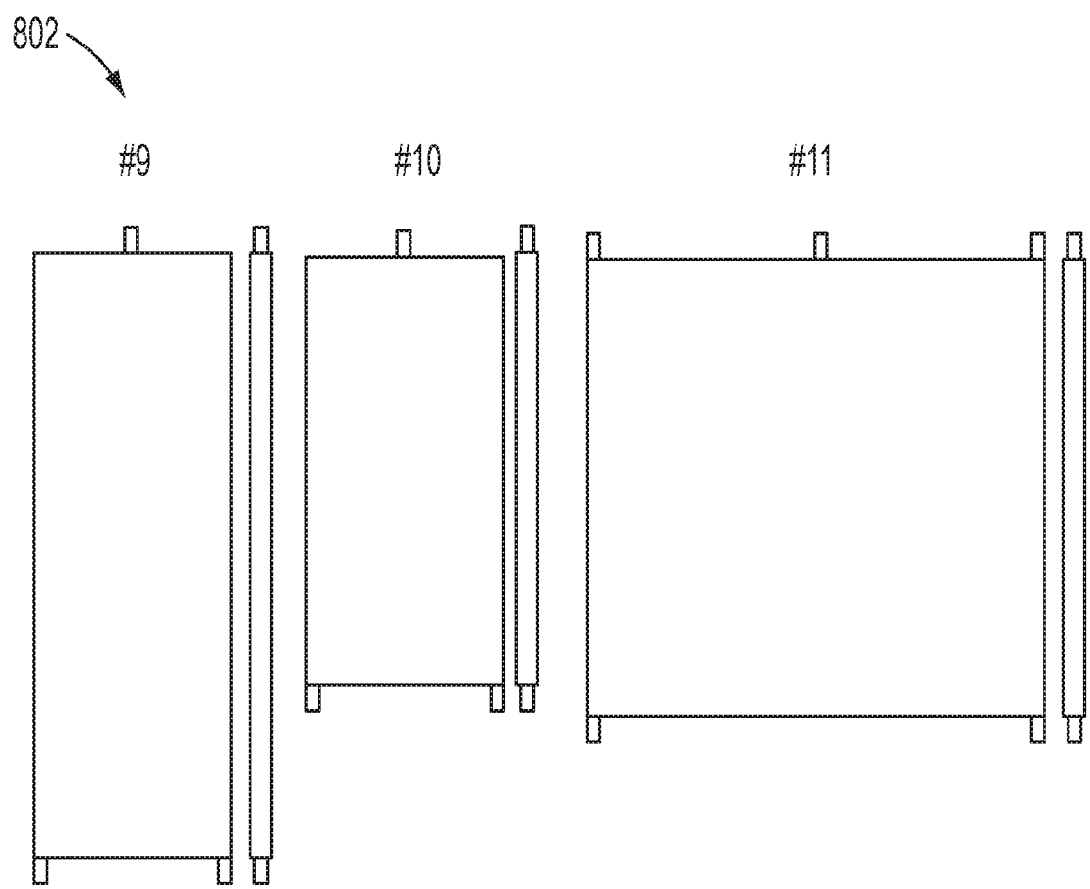
Figure 11:
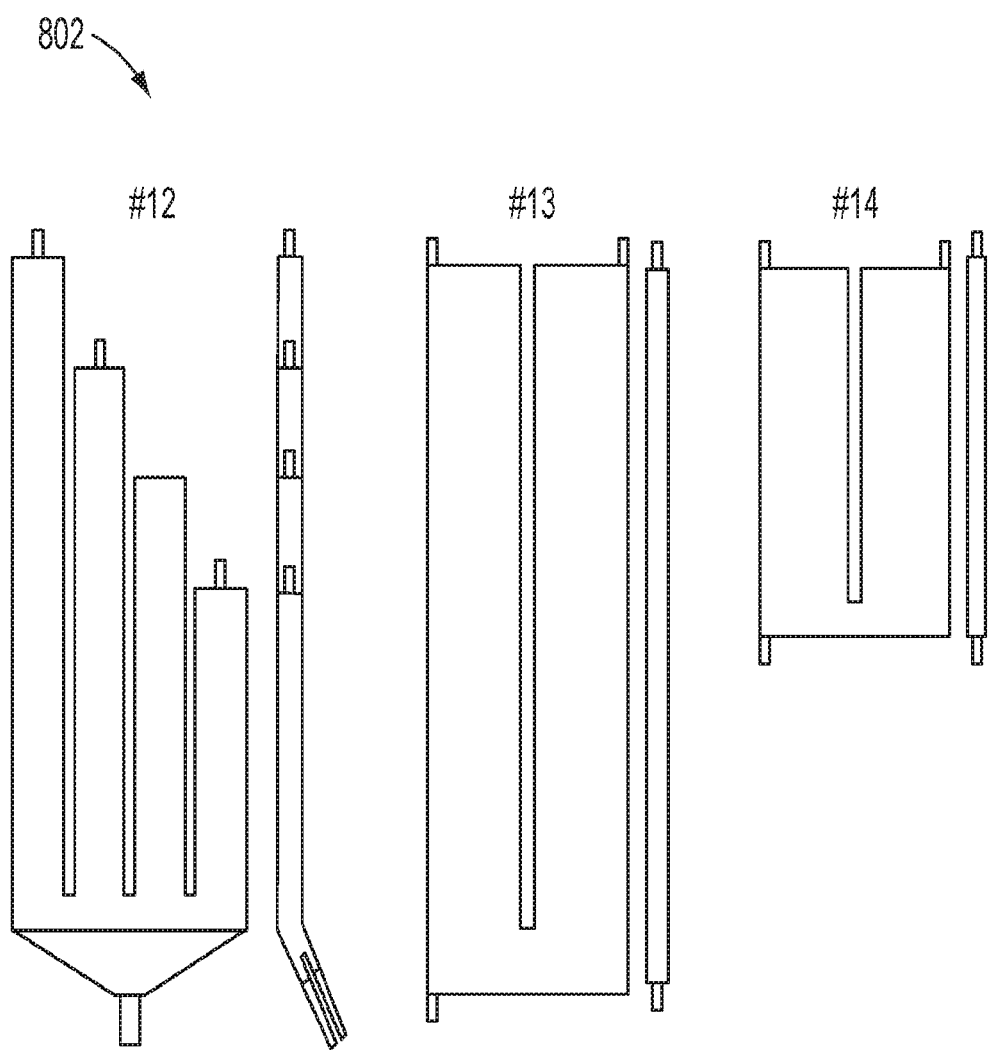
Figure 12:
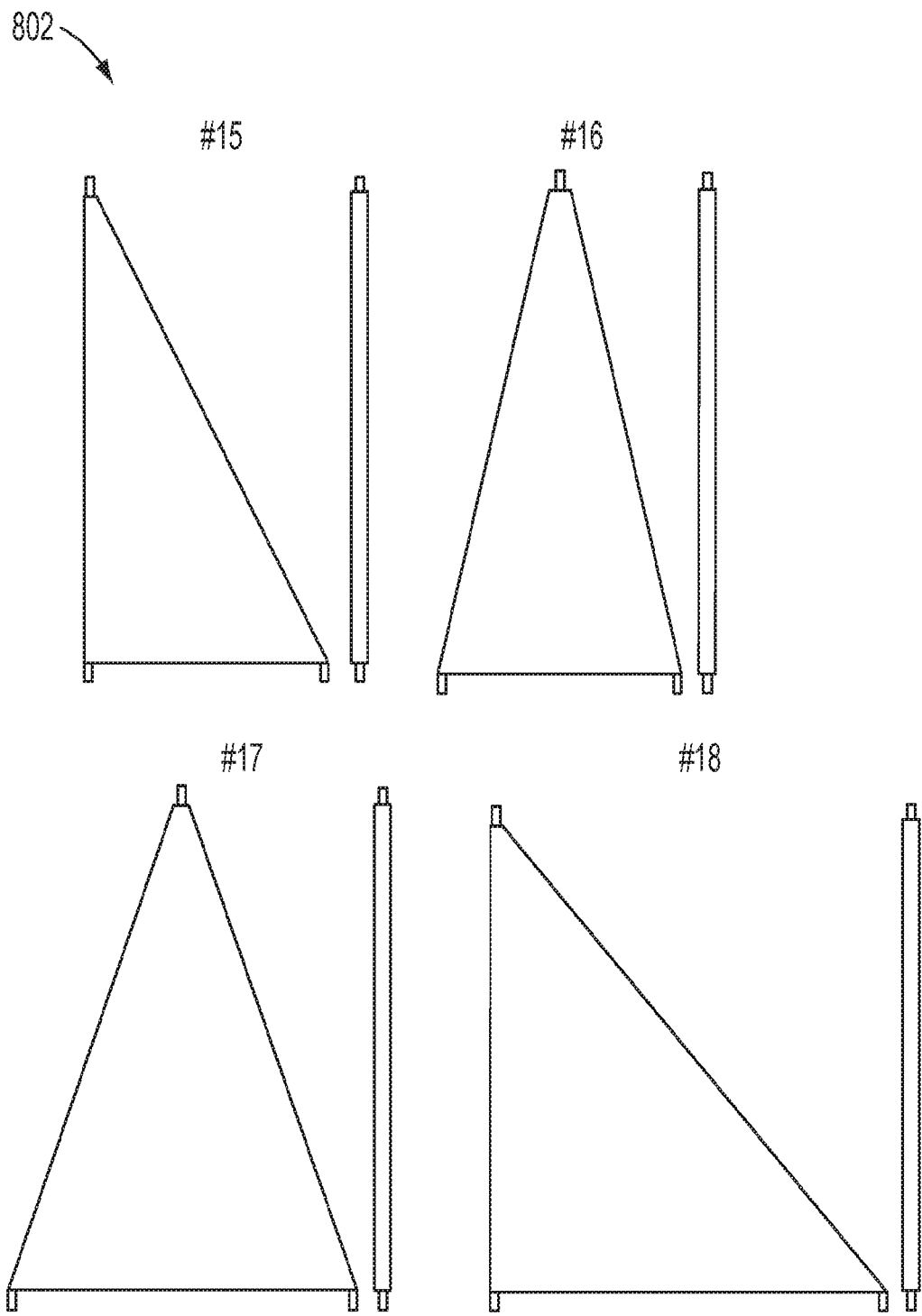

FIG. 7 illustrates a cell separator 700 according to various embodiments. As shown, the cell separator 700 in FIG. 7 is triangular and the previous depictions are rectangular. In some embodiments, the triangular format may achieve the same or similar cell separation efficiency while reducing material requirements.

Figure 16:
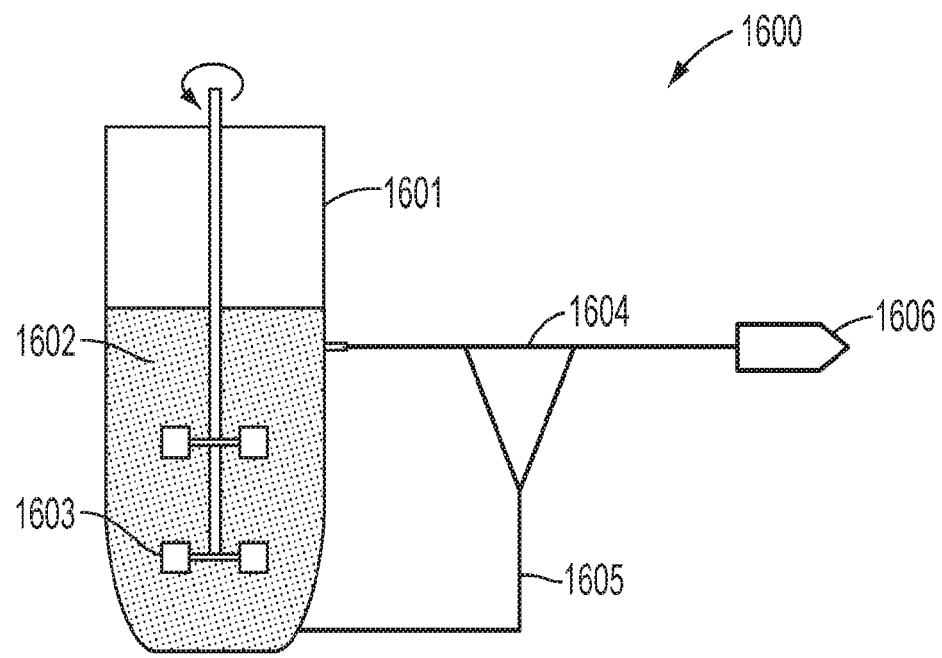
FIG. 16 illustrates results 1600 obtained that correspond to the cell separator designs 802 depicted in FIGS. 8-12.

FIGS. 8-12 illustrate a variety of cell separator designs 802 that were investigated. FIGS. 13-15 illustrate a set of cell separator design details 1302 that correspond to the designs shown in FIGS. 8-12. FIG. 16 illustrates results from data that was collected relating to each of designs 1-18.

FIG. 16 illustrates a perfusion system 1600 according to various embodiments. In various embodiments, the perfusion system may include a bioreactor 1601 capable of mixing a cell suspension 1602 using a mixer 1603 or impeller. In various embodiments, the cell suspension 1602 may exit the bioreactor 1601 and enter a separation device 1604 which may then separate the cell suspension 1602 into a concentrated cell suspension 1605 and a clarified liquid 1606. In some embodiments, the clarified liquid 1606 may contain a product to be harvested and in some embodiments the concentrated cell suspension 1605 may be transferred back into the bioreactor 1601 to continue production of the product. In some embodiments the separation device is a filter, centrifuge, or the gravity based cell settlor/separation device disclosed here.

Figure 17:
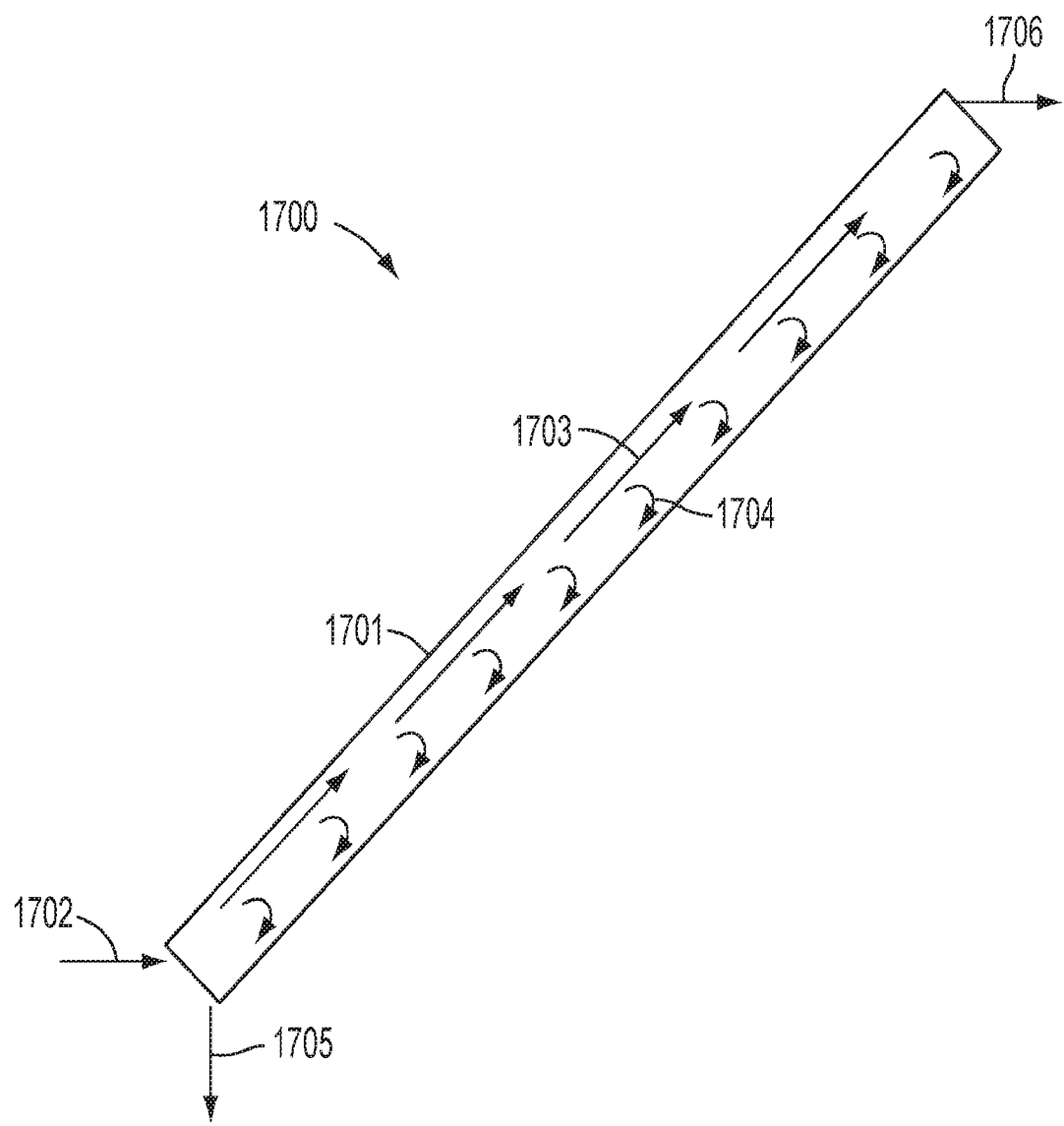
FIG. 17 illustrates a gravity based cell separation device according to the prior art.

FIG. 17 illustrates a prior art embodiment of a separation device 1700. Traditionally, a cell suspension 1702 would enter from the bottom of a settlor chamber 1701 and travel along a primary flow direction 1703. Settling cells 1704 would then start to drop out of the primary flow direction and drop back down toward an exit point for the concentrated cell suspension 1705. Clarified liquid 1706 would exit out the top of the settlor chamber 1701.

Figure 18:
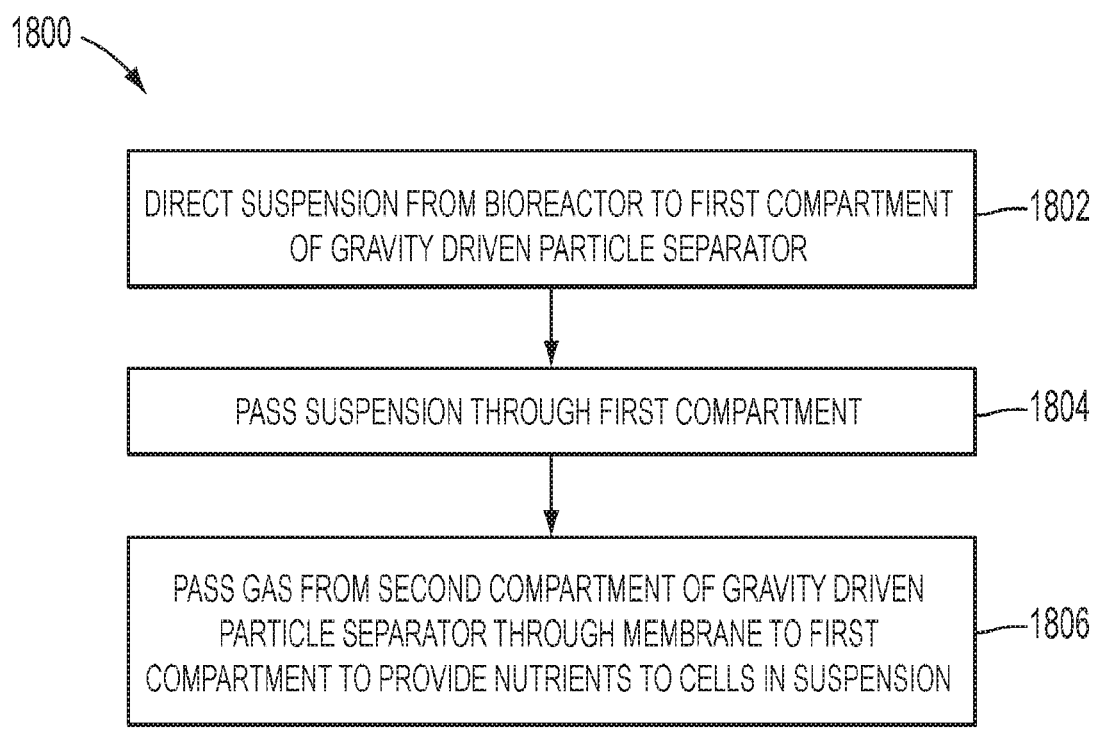
FIG. 18 illustrates a method according to various embodiments.
Figure 19:
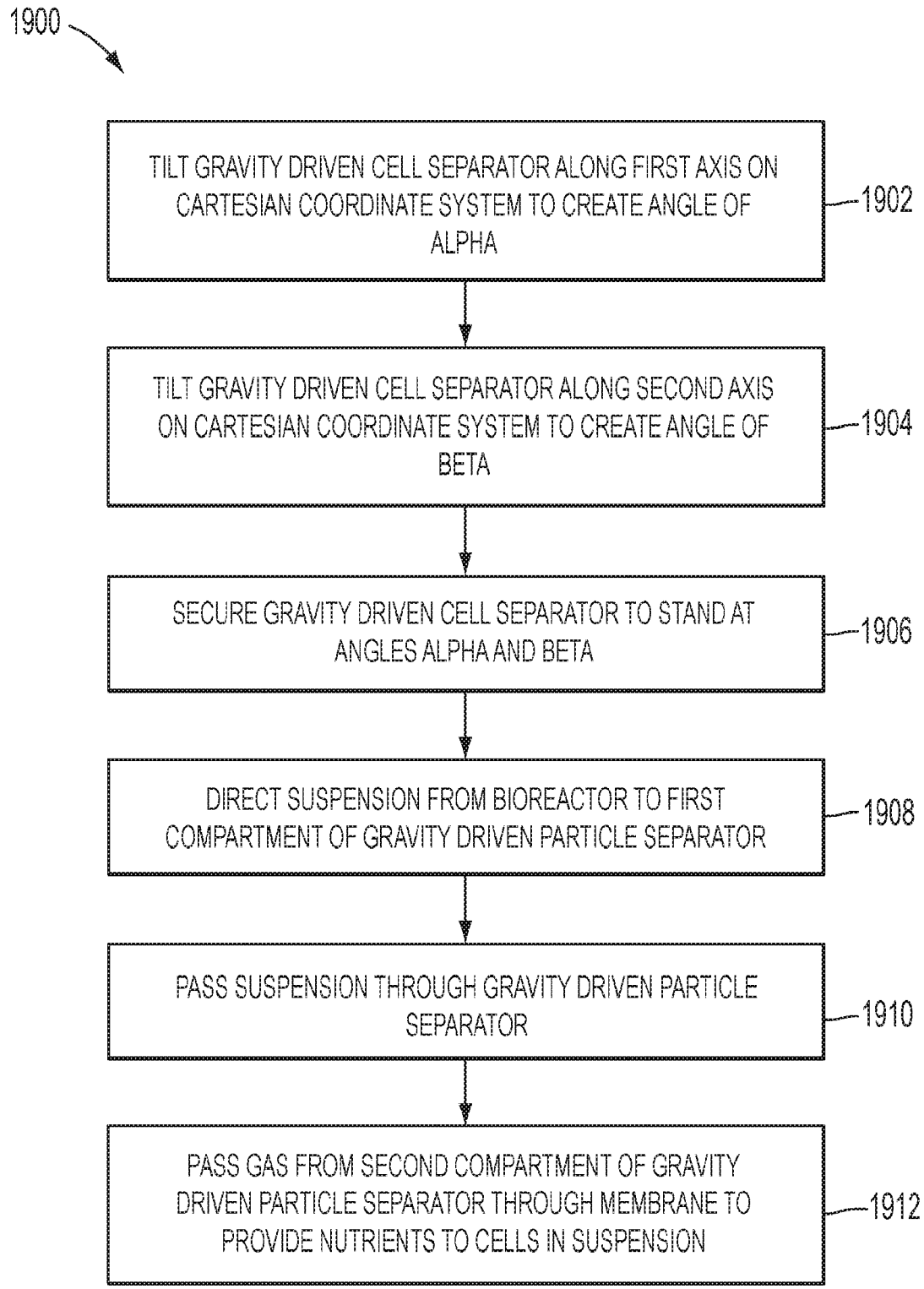
FIG. 19 illustrates a method according to various embodiments.

FIG. 18 illustrates a method of using a gravity driven particle separator 1800 according to various embodiments. Some embodiments include the step of directing a suspension from a bioreactor to a first compartment of a gravity driven particle separator 1802. Some embodiments include the step of passing the suspension through the first compartment 1804. Some embodiments include the step of passing a gas from a second compartment of the gravity driven particle separator through a membrane to the first compartment to provide nutrients to cells in the suspension 1806. Some embodiments include the step of concentrating the cells into a concentrated suspension. Some embodiments include the step of directing a clarified liquid to a first outlet and the concentrated suspension to a second outlet. Some embodiments include the step of directing a portion of the concentrated suspension back to the bioreactor. Some embodiments include the step of cooling the gravity driven particle separator. Some embodiments include the step of heating the gravity driven particle separator.

FIG. 18 illustrates a method of setting up and operating a gravity driven cell separator 1900 according to various embodiments. Some embodiments include the step of tilting a gravity driven cell separator along a first axis on a Cartesian coordinate system to create an angle of alpha 1902. Some embodiments include the step of tilting a gravity driven cell separator along a second axis on a Cartesian coordinate system to create an angle of beta 1904. Some embodiments include the step of securing the gravity driven cell separator to a stand at angles alpha and beta 1906. Some embodiments include the step of directing a suspension from a bioreactor to a first compartment of the gravity driven particle separator 1908. Some embodiments include the step of passing the suspension through the gravity driven particle separator 1910. Some embodiments include the step of passing a gas from a second compartment of the gravity driven particle separator through a membrane to provide nutrients to cells in the suspension 1912. In some embodiments the nutrients include oxygen.

Figure 20:
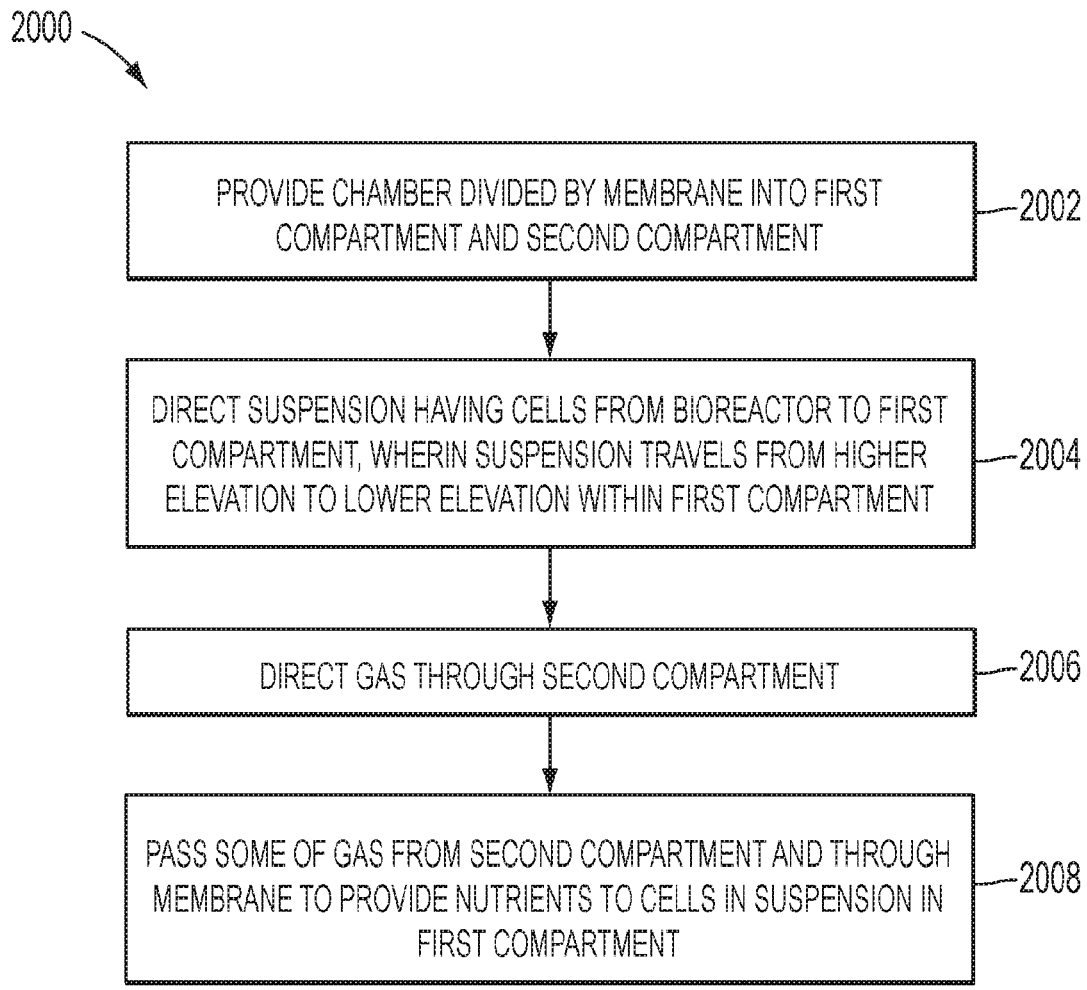
FIG. 20 illustrates a method according to various embodiments.

FIG. 20 illustrates a method of providing nutrients to cells during sedimentation in a gravity driven cell separator according to various embodiments. Some embodiments include the step of providing a chamber divided by a membrane into a first compartment and a second compartment 2002. Some embodiments include the step of directing a suspension having cells from a bioreactor to the first compartment, wherein the suspension travels from a higher elevation to a lower elevation within the first compartment 2004. Some embodiments include the step of directing a gas through the second compartment 2006. Some embodiments include the step of passing some of the gas from the second compartment and through the membrane to provide nutrients to cells in the suspension in the first compartment 2008. In some embodiments, the nutrients include oxygen. In some embodiments, the membrane is supported by a support structure having a plurality of openings.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequences may be varied and still remain within the spirit and scope of the various embodiments.

What is claimed is:

1. A perfusion bioproduction system comprising:
   gravity driven cell separator comprising:
      a chamber divided by a gas permeable membrane into a first compartment and a second compartment;
      a liquid inlet configured to receive a suspension with cells and deliver a clarified liquid to a first liquid outlet and a concentrated suspension to a second liquid outlet; and
      wherein the second compartment comprises a fluid path with a gas inlet and a gas outlet configured to flow gas through the second compartment, the gas permeable membrane and into the first compartment to contact the cells; and
   a stand configured to rotate the gravity driven cell separator at a first angle relative to a first axis of the gravity driven cell separator and at a second angle relative to a second axis of the gravity driven cell separator,
   wherein the gravity driven cell separator is secured to the stand.

2. The perfusion bioproduction system of claim 1, further comprising a bioreactor fluidly connected to the liquid inlet and the second liquid outlet.

3. The perfusion bioproduction system of claim 1, wherein the clarified liquid comprises a product.

4. The perfusion bioproduction system of claim 3, wherein the product is a protein, antibody or enzyme.

5. The perfusion bioproduction system of claim 1, wherein the concentration of cells in the clarified liquid is less than the concentration of cells in the suspension, and the concentration of cells in the suspension is less than the concentration of cells in the concentrated suspension.

6. The perfusion bioproduction system of claim 1, further comprising a support structure with a plurality of openings coupled to the chamber and supporting the gas permeable membrane.

7. The perfusion bioproduction system of claim 1, wherein the gas comprises oxygen.

8. The perfusion bioproduction system of claim 1, further comprising a heating element operably connected to the chamber.

9. The perfusion bioproduction system of claim 1, further comprising a cooling element operably connected to the chamber.

10. The perfusion bioproduction system of claim 1, further comprising a temperature sensor disposed within the chamber.

11. The perfusion bioproduction system of claim 1, wherein the liquid inlet is positioned on the chamber at an elevation above the first and second liquid outlets.

12. The perfusion bioproduction system of claim 1, wherein the first liquid outlet is positioned on the chamber at an elevation above the second liquid outlet.

* * * * *